(12) United States Patent
Greyf et al.

(10) Patent No.: US 10,579,755 B2
(45) Date of Patent: Mar. 3, 2020

(54) METHOD FOR 3-D PRINTING A CUSTOM BONE GRAFT

(71) Applicants: Arthur Greyf, Millburn, NJ (US); Irina Balako, West Windsor, NJ (US)

(72) Inventors: Arthur Greyf, Millburn, NJ (US); Irina Balako, West Windsor, NJ (US)

( * ) Notice: Subject to any disclaimer, the term of this patent is extended or adjusted under 35 U.S.C. 154(b) by 0 days.

(21) Appl. No.: 16/395,273

(22) Filed: Apr. 26, 2019

(65) Prior Publication Data

US 2019/0251217 A1 Aug. 15, 2019

Related U.S. Application Data

(60) Division of application No. 15/285,169, filed on Oct. 4, 2016, which is a continuation-in-part of application
(Continued)

(51) Int. Cl.
*B29C 64/165* (2017.01)
*G06F 17/50* (2006.01)
(Continued)

(52) U.S. Cl.
CPC ............ *G06F 17/5009* (2013.01); *A61F 2/28* (2013.01); *A61F 2/30942* (2013.01); *B29C 64/165* (2017.08); *G05B 19/4099* (2013.01); *A61F 2002/2825* (2013.01); *A61F 2002/2853* (2013.01); *A61F 2002/3092* (2013.01); *A61F 2002/30948* (2013.01); *A61F 2002/30952* (2013.01); *A61F 2002/30957* (2013.01); *A61F 2002/30962* (2013.01); *A61F 2002/30971* (2013.01); *A61F 2240/002* (2013.01); *A61F 2310/00353* (2013.01); *A61F 2310/00359* (2013.01); *B29C 48/02* (2019.02); *B29C 48/266* (2019.02); *B29K 2001/12* (2013.01); *B29K 2029/04* (2013.01); *B29K 2033/12* (2013.01); *B29K 2039/06* (2013.01); *B29K 2067/046* (2013.01); *B29K 2105/0005* (2013.01); *B29K 2105/0011* (2013.01); *B29K 2105/0014* (2013.01); *B29K 2105/0035* (2013.01); *B29K 2105/0088* (2013.01); *B29K 2105/04* (2013.01); *B29K 2995/006* (2013.01);
(Continued)

(58) Field of Classification Search
None
See application file for complete search history.

(56) References Cited

U.S. PATENT DOCUMENTS 10,064,726 B1 * 9/2018 Wei .................. A61F 2/30942
2015/0224226 A1 * 8/2015 Bhatia .................. C12N 5/0068
435/1.1
(Continued)

*Primary Examiner* — Edmund H Lee
(74) *Attorney, Agent, or Firm* — Ashok Tankha

(57) ABSTRACT

A method for producing bone grafts using 3-D printing is employed using a 3-D image of a graft location to produce a 3-D model of the graft. This is printed using a 3-D printer and a printing medium that produces a porous, biocompatible, biodegradable material that is conducive to osteoinduction. For example, the printing medium may be PCL, PLLA, PGLA, or another approved biocompatible polymer. In addition such a method may be useful for cosmetic surgeries, reconstructive surgeries, and various techniques required by such procedures. Once the graft is placed, natural bone gradually replaces the graft.

13 Claims, 11 Drawing Sheets

Related U.S. Application Data

No. 14/447,085, filed on Jul. 30, 2014, now abandoned.

(60) Provisional application No. 61/901,043, filed on Nov. 7, 2013, provisional application No. 61/867,755, filed on Aug. 20, 2013.

(51) Int. Cl.
| | | |
|---|---|---|
| *A61F 2/28* | (2006.01) | |
| *A61F 2/30* | (2006.01) | |
| *G05B 19/4099* | (2006.01) | |
| *B29K 33/00* | (2006.01) | |
| *B29K 1/00* | (2006.01) | |
| *B29K 105/04* | (2006.01) | |
| *B29K 105/00* | (2006.01) | |
| *B29L 31/00* | (2006.01) | |
| *B29K 29/00* | (2006.01) | |
| *B33Y 70/00* | (2020.01) | |
| *B33Y 10/00* | (2015.01) | |
| *B29C 48/25* | (2019.01) | |
| *B29C 48/02* | (2019.01) | |
| *B29K 67/00* | (2006.01) | |

(52) U.S. Cl.
CPC ............ *B29K 2995/0056* (2013.01); *B29L 2031/7532* (2013.01); *B33Y 10/00* (2014.12); *B33Y 70/00* (2014.12); *G05B 2219/45168* (2013.01); *G05B 2219/49023* (2013.01)

(56) References Cited

U.S. PATENT DOCUMENTS

| | | | |
|---|---|---|---|
| 2016/0129637 A1* | 5/2016 | Zhou | G06T 19/20 700/98 |
| 2016/0136887 A1* | 5/2016 | Guillemette | B29C 69/001 428/375 |
| 2017/0057169 A1* | 3/2017 | Grbic | B29C 64/386 |
| 2017/0218228 A1* | 8/2017 | Jose | C09D 11/03 |

* cited by examiner

METHOD FOR 3-D PRINTING A CUSTOM BONE GRAFT

CLAIM OF PRIORITY

This application is a divisional application of U.S. application Ser. No. 15/285,169 filed on Oct. 4, 2016, now abandoned, which claims priority to U.S. application Ser. No. 14/447,085 filed on Jun. 30, 2014, now abandoned, which claims priority to U.S. Provisional Patent Application 61/901,043 filed on Nov. 7, 2013 and to U.S. Provisional Patent Application 61/867,755 filed on Aug. 20, 2013 the contents of all of which are hereby fully incorporated by reference in their entirety.

FIELD OF THE EMBODIMENTS

The field of the invention and its embodiments relate to producing a custom bone graft, and more particularly to methods of producing custom bone grafts or implants using 3-D printing. In particular, the present invention may be useful for reconstructive surgeries and cosmetic surgeries, and any other procedure requiring such augmentation.

BACKGROUND OF THE EMBODIMENTS

Bone grafting is possible because bone tissue, unlike most other tissues, has the ability to regenerate completely if provided the right environment, including a space into which to grow, or a matrix to grow on. As native bone grows, it replaces the graft material, so that over time, the graft is replaced by a fully integrated region of new bone.

Bone regeneration occurs through osteoinduction, a process in which connective tissue is converted into bone by an appropriate stimulus. Osteoinduction allows bone formation to be induced even at non-skeletal sites and is initiated by bone morphogenetic proteins (BMP).

The ideal bone graft material would be a strong, porous biocompatible material infused with BMP that did not cause inflammation and would ultimately be reabsorbed into the body as it is replaced by natural bone.

Bone is composed of 50 to 70% inorganic mineral, 20 to 40% organic collagen matrix, 5 to 10% water, and <3% lipids. The inorganic mineral content of bone is mostly hydroxyapatite $[Ca_{10}(PO_4)_6(OH)_2]$. The inorganic mineral provides the mechanical strength and rigidity, whereas the organic collagen matrix provides elasticity and flexibility.

Demineralized bone matrix (DBM) is allograft bone, i.e., bone from other humans, that has had the inorganic, mineral material removed, leaving behind the organic collagen matrix and the BMPs that induce osteoinduction. DBM is conducive to osteoinduction, but lacks the load bearing strength. It is typically used with a 2-4% hyaluronate carrier as a paste or putty to fill a space needing bone, and allows real bone to grow into it within weeks to months.

The present invention provides a system and method of producing custom bone grafts that are made of a porous, biocompatible material infused with BMPs that can be used as ink in a 3-D printer to produce bone grafts of any desired shape.

Review of Related Art

U.S. Patent Application 2011/0151400 published by A. Boiangiu et al. on Jun. 23, 2011 entitled "Dental Bone Implant, Methods for Implanting the Dental Bone Implant and Methods and Systems for Manufacturing Dental Bone Implants" pertains to a dental bone implant having a first fitted bone graft sized and shaped to fit tightly to a buccal surface of a periodontal alveolar bone around at least one tooth and to reconstruct at least a portion of one or more periodontal bone defect and a second fitted bone graft sized and shaped to fit tightly to a lingual/palatal surface of a periodontal alveolar bone around at least one tooth and to reconstruct at least an additional portion of at least one periodontal bone defect. The portion and the other portion complementary cover the one or more periodontal bone defects.

U.S. Patent Application 2004/0120781 published by S. Luca et al. on Jun. 24, 2004 entitled "Customized instruments and parts for medical-dental applications and method and blank for on-site machining of same" pertains to a customized prosthesis, or instrument, for medical/dental applications which replicates the desired bone-graft, tooth, or tool, being replaced. The dimensions of the prosthesis, or instrument, are determined by mathematically interpolating key-points that characterize a specific part. A computer controlled machine then cuts the desired part out of a pre-fabricated blank, directly at the site of operation. Methods of the invention relate to selecting the type of part being replaced, identifying and measuring the coordinates of key-points for that part, and initializing the automated machining process. Also, special supporting devices that include pre-fabricated features common between certain parts are used in order to facilitate the machining process. The identification of key-points is done by comparing a schematic drawing of the type of part being replaced to the actual part. A grid is then used to measure the coordinates for those key-points.

U.S. Pat. No. 6,671,539 issued to Gateno et al. on Dec. 30, 2003 entitled "Method and apparatus for fabricating orthogenetic surgical splints" pertains to a method of forming a surgical splint to receive a patient's dentition and thereby align the upper jaw and the lower jaw during surgery includes generating a CT computer model of bone structure, generating a digital dental computer model of the patient's dentition, and then combining the CT computer model and the digital dental computer model to form a composite computer model. The composite computer model may be displayed, and at least one of the upper jaw and lower jaw repositioned relative to the patient's skull and the composite computer model to form a planned position computer model. Using this desired position computer model, a computer model surgical splint of the patient's dentition may be formed, which is then input into a fabrication machine to form a surgical splint. The method also includes forming and displaying the composite computer model. A workstation includes a CT machine, a digital scanner, a computer, an input command mechanism, a display, and a fabricating machine.

U.S. Pat. No. 8,021,154 issued to Holzner et al. on Sep. 20, 2011 entitled "Method for manufacturing dental prostheses, method for creating a data record and computer-readable medium" pertains to a method for manufacturing one or several dental prostheses, comprising the steps of: performing a rapid prototyping method for manufacturing one or several dental prostheses and subsequent working, such as reworking, of the one or several dental prostheses with a machining method, such as a milling method. In addition, a method for creating a data record which can be used for a rapid prototyping method for manufacturing a dental prosthesis wherein an end data record is obtained from a starting data record, so that in at least one area of a dental prosthesis manufactured with the end data record excess material is provided, compared to a dental prosthesis manufactured with the starting data record.

Various implements are known in the art, but fail to address all of the problems solved by the invention described herein. One embodiment of this invention is illustrated in the accompanying drawings and will be described in more detail herein below.

SUMMARY OF THE EMBODIMENTS

The present invention describes systems and methods for producing a custom bone graft for at least reconstructive and cosmetic surgeries. The present embodiments may be particularly useful for "donut" type implant insertions and for printing grafts for sinus lifts.

In one embodiment of the present invention there is a method for producing a custom bone graft, comprising: obtaining a 3-D image of an intended graft location; creating a 3-D mesh using said 3-D image; creating a 3-D digital model of said custom bone graft using said 3-D image; and creating, using said 3-D digital mold and a porous, biodegradable, biocompatible material that is conducive to osteoinduction and has a load bearing strength comparable to bone, to produce said custom bone graft.

In another embodiment of the present invention there is a method for producing a custom bone graft, comprising: obtaining an image of an intended graft location; creating a digital model of said custom bone graft using said image; and creating, using a 3-D printer said custom bone graft using a printing medium that forms a porous material that has a load bearing strength comparable to bone.

In one preferred embodiment, a 3-D image of an intended graft location may be obtained. This may be achieved by a number of methods, some of which may be discussed in further detail later. Use may, for instance, be made of 3-D image construction techniques such as, but not limited to, obtaining multiple 2-D X-ray images at different orientations, and using computational techniques to convert these into a 3-D image, using a Cone beam imaging device or a cat-scan device, or some combination thereof.

This 3-D image of the graft location may then be converted into a 3-D digital image of the custom bone graft.

The custom bone graft may be printed directly using a modified 3-D printer and an ink that transforms into a suitable porous, biocompatible, biodegradable material that is conducive to osteoinduction and has a load bearing strength comparable to bone.

The custom bone graft may also or instead be made by using a 3-D printer to print a negative form or mold, and the mold may then be used to produce the custom bone graft. In such a process, in a preferred embodiment, the mold may be filled with a mixture of, for instance, Calcium Sulfate hemihydrate, aka Plaster of Paris, demineralized freeze dried bone (DFDB), or freeze dried bone (FDB), Bone Morphogenetic Proteins (BMP) and an antibiotic such as, but not limited to, Doxycycline.

In a preferred embodiment, the porous, biocompatible material may be porous Poly Methyl Methacrylate (PMMA) and demineralized allograft bone matrix (DMB). The ink for this material may, for instance, be provided as a precursor powder, and a precursor liquid. The precursor powder may, for instance, include demineralized allograft bone matrix (DMB), sucrose crystals and a radical polymerization initiator. The precursor liquid may, for instance, include Methyl Methacrylate (MMA) as well as one or more antibiotics and one or more radio-pacifiers, i.e., compounds that make the graft more radio opaque, or radio dense, so that it may be more visible on X-ray images.

In a preferred embodiment, the radical polymerization initiator may be benzoyl peroxide, the antibiotic may be gentamicin and the radio-pacifier may be barium sulphate.

The precursor liquid and powder may be mixed in small batches to produce the ink just before printing. Once the precursors are mixed the MMA may start to polymerize to PMMA. The viscosity of the liquid will increase with time, but suitably proportioned, the ink may be delivered through a 10-14 gauge needle or print nozzle for about 10 to 20 minutes. This may provide a dot size of about 2 mm in diameter, which may be the resolution of the finest detail of the custom bone graft.

The sucrose crystals provide the porosity to the structure when they are dissolved out in post print processing.

The structure printed by the ink may also be made biodegradable by the inclusion of cellulose acetate (CA) or cellulose acetate phthalate (CAP), or a combination thereof. The biodegradability may allow the porous PMMA structure to be replaced by natural bone over time.

Therefore, the present invention succeeds in conferring the following, and others not mentioned, desirable and useful benefits and objectives.

It is an object of the present invention to provide custom bone grafts suitable for use in disciplines such as, but not limited to, Orthopedics, Plastic Surgery, ENT and Dentistry.

It is a further object of the present invention to be of use in procedures, including plastic surgery procedures, such as, but not limited to, cleft palate surgical repair, facial and non-facial post trauma or tumor removal reconstruction.

It is an object of the present invention to provide a method of producing custom bone grafts at a reasonable price.

It is a further object of the present invention to provide bone grafts that may be an intimate fit to the graft site, as this may increase the chances of bone graft maturation and healing, and because intimate contact is one predictor of a successful surgery.

It is another object of the present invention to provide a method of producing a custom bone graft using equipment that may be located at a surgeon, or plastic surgeon's, site or office.

It is an object of the present invention to provide suitable ink for use in suitably modified 3-D printers.

It is a further object of the present invention to design and fabricate bone grafts to add lost tissue or tissue that was never developed.

It is a further object of the present invention to design and fabricate grafts for a sinus lift.

It is a further object of the present invention to design and fabricate implants for cosmetic procedures.

It is a further object of the present invention to provide grafts and/or implants for reconstructive surgery.

It is a further object of the present invention to provide for donut-type insertions of implants and/or grafts.

It is a further object of the present invention to provide a printing method that uses extrusion of the printing medium.

DESCRIPTION OF THE PREFERRED EMBODIMENTS

Figure 1:
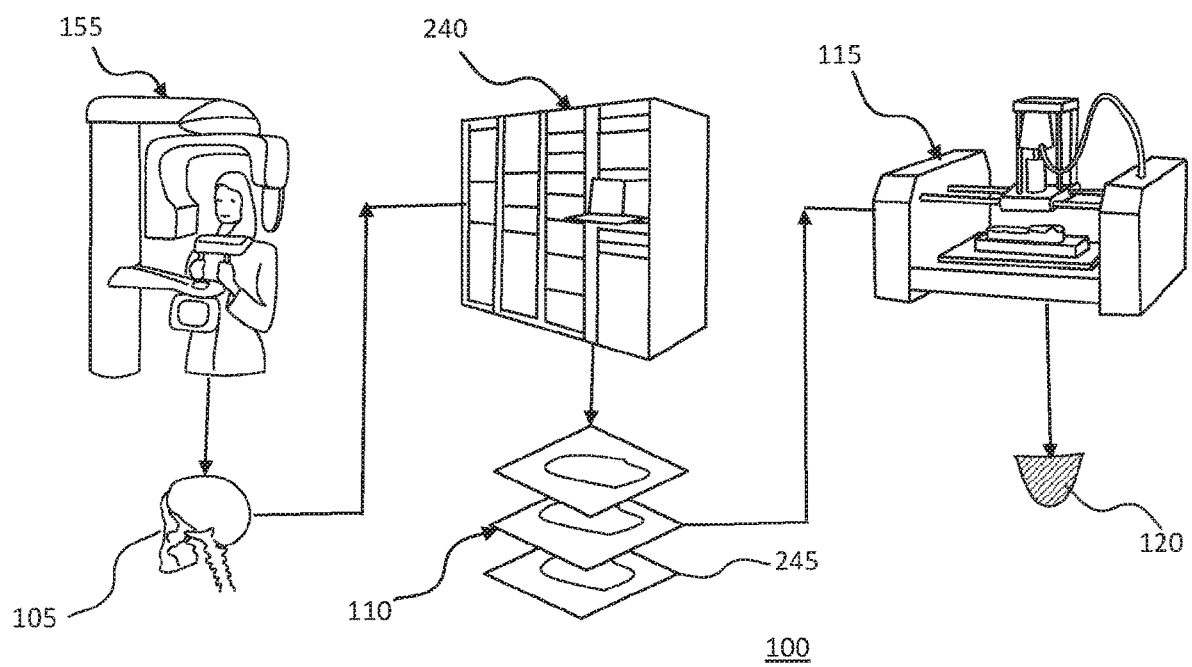
FIG. 1 shows a preferred embodiment of a method for producing a custom bone graft.

The preferred embodiments of the present invention will now be described with reference to the drawings. Identical elements in the various figures are identified with the same reference numerals.

Various embodiments of the present invention are described in detail. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 shows a preferred embodiment of a method for producing a custom bone graft. An X-ray imaging machine 155 may be used to take one or more images of a region of a patent where a custom bone graft 120 may be needed. These may then be assembled into a 3-D image 105 of the region requiring a custom bone graft 120. A suitably programmed digital processor 240 may take the 3-D image 105 and transform it into a 3-D model of the region requiring the custom bone graft 120. This 3-D model may then be used to generate a 3-D model of the required custom bone graft 120. This 3-D model of the required custom bone graft 120 may then be used by a software module operative on the digital processor 240 to generate instructions for a 3-D printer 115. These instructions may, for instance, take the form of a 3-D digital model 110 made up of a series of layers 245. These layers of a 3-D digital model 245 may, for instance, be sized to the resolution of the 3-D printer 115 that may be used to generate the custom bone graft 120.

The 3-D printer 115 may be configured to apply the printing medium or ink, as noted above, in layers or a series of layers. In some embodiments the 3-D printer 115 may operate using an extrusion deposition method, fusing of granular materials, lamination methodologies, photopolymerization methodologies, or continuous liquid interface production methodologies. Preferably, the 3-D printer 115 has a compound heating element which comprises at least two components: 1) printer portion and 2) application or syringe portion. This allows for extrusion printing techniques to be accomplished and the use of compatible materials for such techniques.

The 3-D printer 115 may then be used to produce the custom bone graft 120 layer by layer using an appropriate ink, or series of inks. The 3-D printer may have a number of parts/components including an infection control mechanism to prevent contamination of the printed graft and the printer components. Preferably there is a hood or venting hood which can be closed over and around the printing mechanism that is coupled to a medical grade HEPA filter. Sterile or clean air can then be drawn into the hood via the HEPA filter and removed via a surgical-type suction connection. Such a process will prevent or limit the chance of contamination of the graft and printing components/surfaces with pathogens.

In one embodiment, a 3-D printer 115 uses a syringe 500 (see FIG. 15) to apply the printing material. The syringe may come in varying sizes such as 0.5 cc, 1.0 cc, 1.5 cc, 2.0 cc, 2.5 cc, and 3.0 cc. In some embodiments, different sizes, including those over 3.0 cc may be employed.

Figure 15:
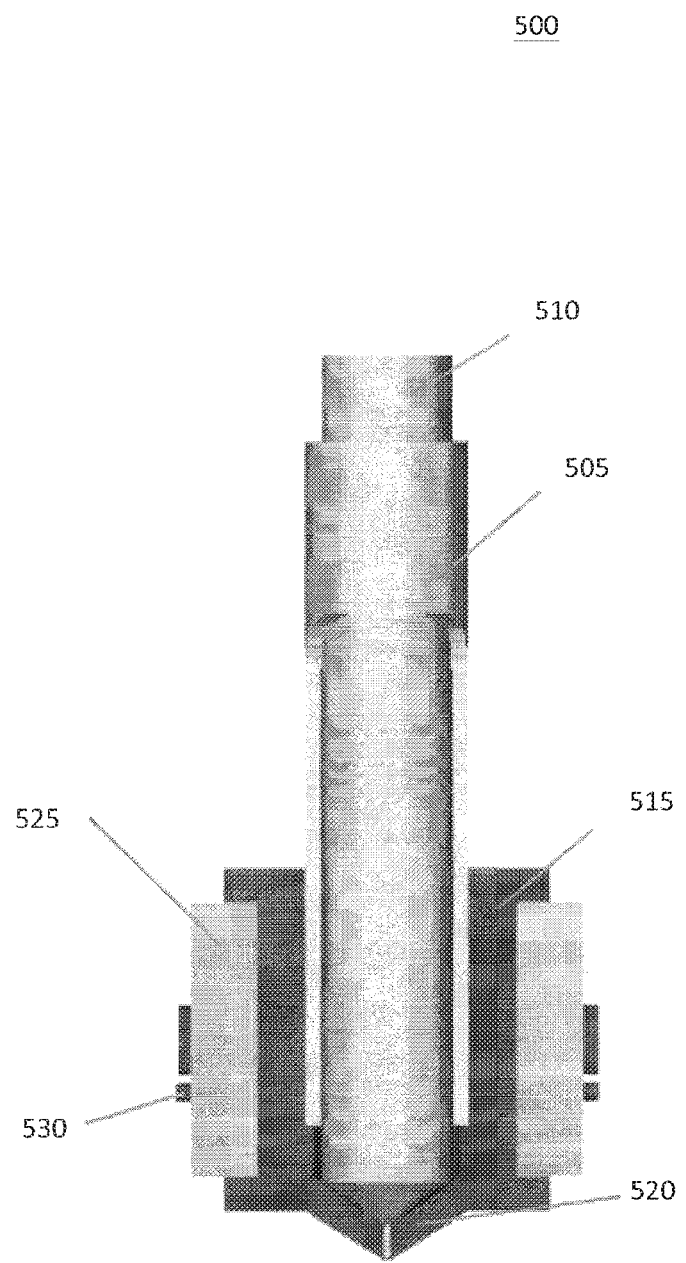
FIG. 15 illustrates a sectional side view of an embodiment of a syringe in accordance with the present invention.

Referring now to FIG. 15, the syringe 500 (shown in a sectional sideview) preferably has a plunger (not shown) comprised of at least one FDA approved material and a barrel 505 coated with or comprised wholly of Teflon® or other low friction FDA approved material(s). This composition/coating helps to allow for full extrusion of the printing material/medium 510 or ink from the syringe 500. Further, the plunger may vary in size, in relation to the size of the barrel, to effectuate this full extrusion. The plunger or piston may be advanced or retracted by the printer.

The syringe 500 is intended to be a single or one time use syringe, and is preferably kept under sterile conditions (e.g. packaging) until the graft is ready to be printed. Such a syringe 500 is fully assembled (plunger, printing medium contained within barrel, etc.) and ready for use out of the packaging. In some embodiments, chips, codes (bar code, QR code, etc.) may be used to identify/verify the syringe and its contents before use.

In some embodiments, the printing material 510 may be in the form of a solid "rod" which is heated by at least one heating element allowing the solid or semi-solid printing material 510 to be extruded by increasing a temperature of the material to approximately its melting point. Thus, the syringe 500 has a heated head or tip 520 that allows more viscous or solid or semi-solid printing materials to be easily extruded through the syringe tip 520. This heated head is preferably made of a metal or metals with the nozzle or tip being shaped to allow the printing material or ink to pass therethrough. The heated head 515 is heated via a heating mechanism 525 of the 3-D printer. The heated head 515 allows for heat to be transferred or conducted thereby causing the printing medium 510 to soften or melt. The heating mechanism further has temperature sensors or thermostats 530 that will provide feedback to the printer/ software allowing for modifications to temperature to be made in real time throughout the printing process.

A locking mechanism will ensure that an operable connection is established and maintained between the headed head of the syringe 500 and the heating mechanism 525 of the printer. The locking mechanism may be a latch or lock that can be electronically or manually positioned. In other embodiments, the locking mechanism is defined by a shape of the heated head and a complementary shape of the heating mechanism which interact to provide this locking feature.

The syringe "pump" or piston is preferably comprised of an FDA approved material and mechanism. This may comprise hydraulics, mechanical movements, or some combination thereof. The syringe may be coupled to the printer via a robotic arm and may use magnets to allow for easy changing of the syringe.

In a preferred embodiment the printing medium or inks include polycaprolactone (PCL), polylactic acid (PLLA), polylactic-co-glycolic acid (PLGA) or other FDA approved biodegradable materials. Preferably the printing medium is PCL.

Referring now back to FIG. 1, in at least one embodiment, the printing is done in an offset grid configuration to allow for blood vessel growth and permeation through the graft and/or implant. This is achieved by side stepping or rotating of the direction of the printed layers. Such a printing configuration allows for up to 100% penetration of the grafting material(s) and any required medications.

The surface of the printer, on which the graft is printed, is preferably a sterile, disposable printing surface. In at least one embodiment the printing surface or tray is comprised of boric silica glass with a polyethylene terephthalate (PET) coating. The size of the tray may vary but is preferably about 100 mm times.100 mm. The tray may also be thermally manipulated to meet certain temperature conditions.

The tray or surface (disposable plate) may be supplied in a sterile packaging (similar to the syringe) to be affixed to the printer prior to the printing process. It is desirable that the printing medium will slightly adhere to the printing surface or tray to prevent movement of the graft while printing. However, once completed, the graft must also be able to be easily freed from the printing tray.

In a preferred embodiment, the X-ray imaging machine 155 may be a Cone Beam 3 D camera such as, but not limited to, the model GX DP-700 supplied by Gendex Dental Systems of Hatfield, Pa. In other embodiments, other imaging devices may be used such as, but not limited to, other computer aided tomography devices, cat-scan devices, 3-D laser cameras or a combination thereof.

Figure 2:
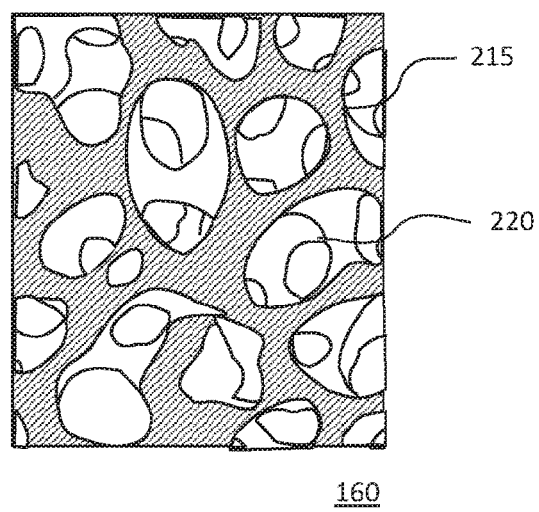
FIG. 2 shows a magnified section of the mineral structure of bone.

FIG. 2 shows a magnified section of the mineral structure of bone. Mammalian bone may be composed of a bone mineral 215 having a lattice or matrix of voids 220. Bone may typically be composed of 50 to 70% inorganic mineral, 20 to 40% organic collagen matrix, 5 to 10% water, and <3% lipids. The organic collagen, water, lipids and blood vessels are typically contained within the voids. The inorganic mineral content of bone is mostly hydroxyapatite [$Ca_{10}(PO_4)_6(OH)_2$]. The inorganic mineral provides the mechanical strength and rigidity, whereas the organic collagen matrix provides elasticity and flexibility.

Figure 3:
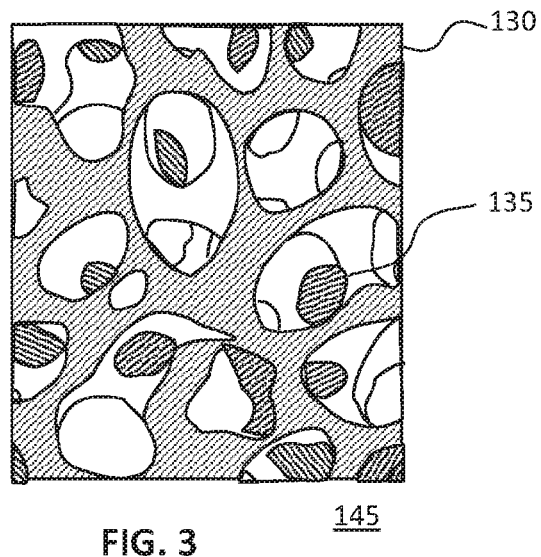
FIG. 3 shows a magnified section of a demineralized allograft bone matrix (DMB).

FIG. 3 shows a magnified section of a demineralized allograft bone matrix (DMB). The demineralized allograft bone matrix (DMB) 145 may be made up of collagen 130, typically formed into a matrix structure, and bone morphogenetic proteins (BMP) 135. Bone morphogenetic proteins (BMPs) are a group of growth factors also known as cytokines and as metabolomes. They were originally discovered through their ability to induce the formation of bone and cartilage, and are now considered to constitute a pivotal group of morphogenetic signals that may orchestrate tissue architecture throughout the body. Although bone morphogenetic proteins (BMP) 135 may be manufactured by genetic engineering, demineralized allograft bone matrix (DMB) 145 is a favored source, and may be used in a paste or putty to facilitate bone regeneration. Demineralized allograft bone matrix (DMB) 145, i.e., allograft bone that has had inorganic minerals removed, may expose more bone morphogenetic proteins (BMP) 135 and therefore facilitate faster growth of natural bone into the paste or putty. Demineralized allograft bone matrix (DMB) 145 does not, however, have the strength of natural bone. Allograft bone is human bone, typically taken from cadavers and bone banks.

Demineralized allograft bone (DMB) 145 may be obtained from, for instance, MAXXEUS Inc., of Kettering, Ohio who sells it under the brand name MAXXEUS™ DBM PUTTY.

Figure 4:
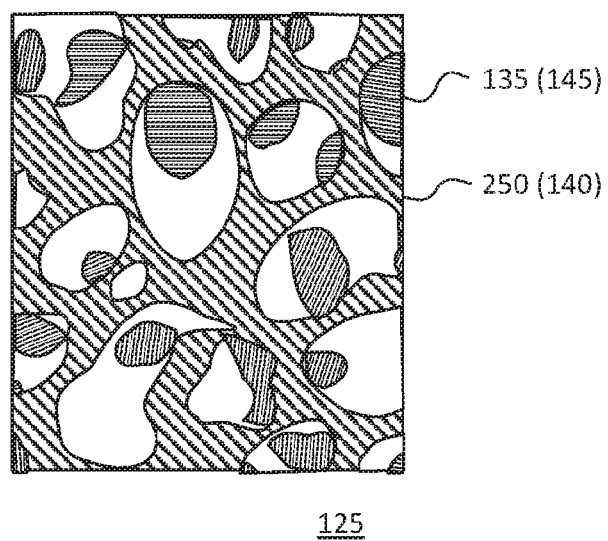
FIG. 4 shows a magnified section of a porous, biocompatible material suitable for use as a bone graft.

FIG. 4 shows a magnified section of a porous, biocompatible material suitable for use as a bone graft. The porous, biocompatible material 125 may, for instance, be made up of a biocompatible, porous structural support 250 made conducive to osteoinduction by the presence of bone morphogenetic proteins (BMP) 135.

In a preferred embodiment, the biocompatible, porous structural support 250 may, for instance, be porous Poly Methyl Methacrylate (PMMA) 140 and the bone morphogenetic proteins (BMP) 135 may, for instance, be demineralized allograft bone matrix (DBM) 145. The bone morphogenetic proteins (BMP) 135 may also, or instead, be a synthetically produced compound such as, but not limited to, recombinant human Bone Morphogenetic Protein-2 (rh-BMP-2) as provided by, for instance, Medtronic Inc. of Minneapolis, Minn. in their INFUSE Bone Graft material.

Poly Methyl Methacrylate (PMMA) 140 is a synthetic polymer of methyl methacrylate, whose biocompatibility was, apparently, discovered by accident during WWII when RAF pilots suffered eye injuries from the destruction of their side widows. Hawker Hurricane pilots, whose windows were made of glass, suffered severe rejection/infection in the vicinity of the glass splinters in their eyes, while Spitfire pilots, whose side windows were made of PMMA suffered no rejection/infection in the vicinity of the PMMA splinters. This good degree of compatibility with human tissue has been exploited by using PMMA for intraocular eye lenses that replace cataract damaged lenses, and in orthopedic surgery. In orthopedic surgery it is used as a grout, or bone cement, to stabilize join implants. PMMA bone cement such as, but not limited to, SIMPLEX P™ BONE CEMENT sold by the Stryker Corporation of Kalamazoo, Mich. is typically supplied as a powder and a liquid. The ingredients of Stryker's SIMPLEX P™ BONECEMENT are reported to be 75% methyl methacrylate; 15% polymethylmethacrylate (PMMA); 10% Barium Sulfate for radio-opaqueness, and an undisclosed quantity of benzoyl peroxide to initiate the radical induced polymerization of the MMA to PMMA. The amount of the radical polymerization initiator, benzoyl peroxide, may be crucial for determining the mixing, handling, and setting characteristics of the bone cement.

In orthopedic use, the powder and liquid precursors are mixed about 10 minutes before being used. Mixing the powder and liquid initiates the polymerization, which may take up to several hours to complete. They are either applied as putty, or delivered to the required site by means of needles that range in size from 10 to 14 gauges, i.e., in the vicinity of 2 mm internal bore needles.

Figure 5:
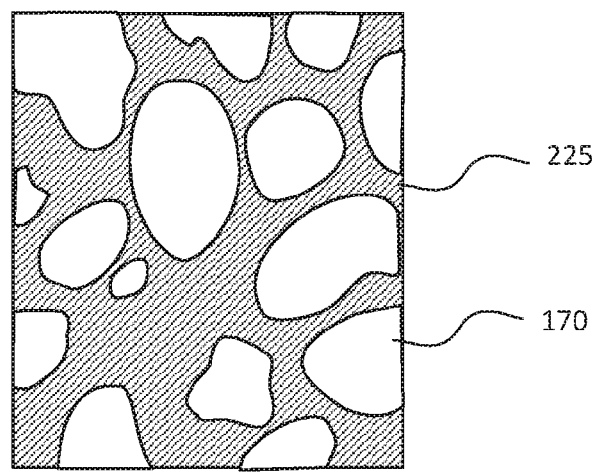
FIG. 5 shows a magnified section of an intermediate stage in producing porous Poly Methyl Methacrylate (PMMA).

FIG. 5 shows a magnified section of an intermediate stage in producing porous poly methyl methacrylate (PMMA).

The porous Poly Methyl Methacrylate (PMMA) 140 may be produced by including sucrose crystals 170 of the appropriate size in the MMA being polymerized. After the MMA is fully polymerized from its liquid form to solid form, the sucrose crystals 170 may be dissolved out, leaving behind a porous PMMA structure.

This method of producing a porous PMMA structure was developed in order to overcome some shortcomings of existing PMMA bone cement, as reported by A. Rijke et al in an article entitled "Porous Acrylic Cement" published in J Biomed Mater Res. 1977 May; 11(3):373-94, the contents of which are hereby incorporated by reference.

Shortcomings of PMMA bone cement include that it heats up to 82.5.degree. C. (160.5.degree. F.) while setting. This is high enough to cause thermal necrosis of neighboring tissue, or any biomaterial such as, but not limited to, collagen and bone morphogenetic proteins (BMP) that may be found in demineralized allograft bone matrix (DMB).

By modifying the cement composition through the addition of soluble, nontoxic filler such as sucrose or tri-calcium phosphate which does not impair the workability of the material during surgery, a significant improvement in the performance of the cement can be achieved. Because the filler replaces part of the acrylic components, less heat is generated during curing while the filler itself acts as a heat sink.

Porous cement may be obtained provided that a critical minimum percentage loading of the filler is exceeded so that the filler crystals will make physical contact with each other. The value of this percentage depends on both crystal modification and size. With crystals in the 125-175 micron range, the critical minimum percentage may be in the range of 20-28 wt. % loading. Above 30%, the interconnecting pore size increases and may allow good tissue ingrowth into the pores. The introduction of filler and pores may cause a drop in strength, but the tensile strength of modified cement containing up to 40% pores and sucrose lies between 0.7 and 1.5 kg/mm sup.2, which is in the same range as that of bone.

Poly methyl methacrylate (PMMA) may be made biodegradable by the addition of cellulose acetate (CA) 255 or cellulose acetate phthalate (CAP) 260, as described in, for instance, an article by D. Batt et al. entitled "Biodegradability of PMMA Blends with Some Cellulose Derivatives", published in Journal of Polymers and the Environment, October 2006, Volume 14, Issue 4, pp. 385-392, the contents of which are hereby incorporated by reference.

The rate of biodegradation may be controlled by the relative amount of the compound use to increase the biodegradability of the ink, or the product produced by the polymerized ink.

Figure 6:
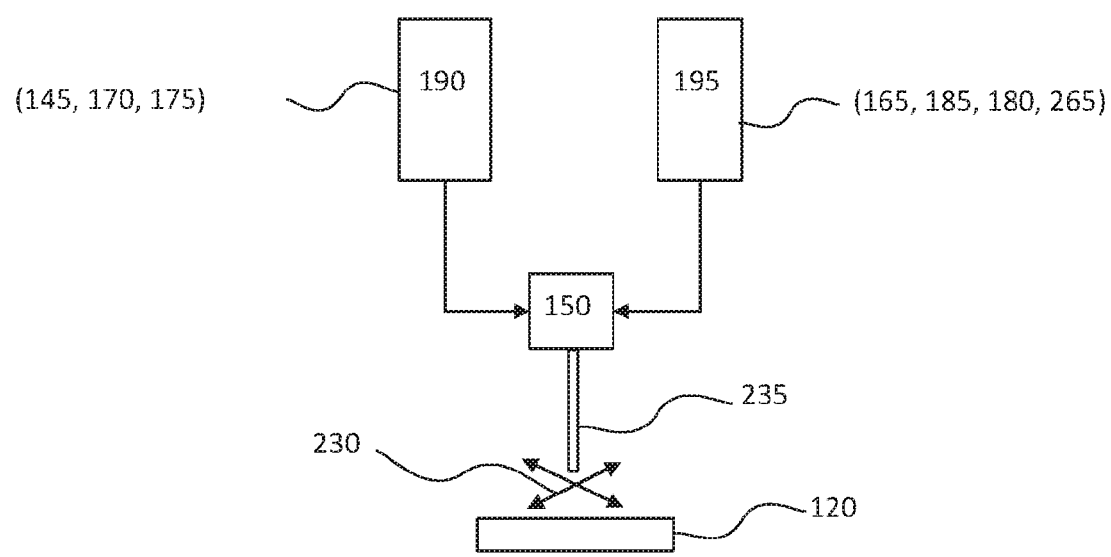
FIG. 6 shows a sematic layout of the ink mixing and print nozzle of a preferred embodiment of the present invention.

FIG. 6 shows a sematic layout of an ink mixing and print nozzle of a preferred embodiment of the present invention.

In a preferred embodiment, the ink may contain structural material ingredients; ingredients to form a porous, resorbable, matrix; and additives such as, but not limited to, synthetic BMPs, antibiotic chemicals, anti-inflammatory chemicals and radiopaque chemicals, or some combination thereof.

The structural material ingredients may, for instance, include a substance such as, but not limited to, Hydroxyapatite, allograft particulate bone, xenograft particulate bone or some combination thereof.

The ingredients to form a porous, resorbable matrix may include substances such as, but not limited to, methyl methacrylate, cellulose, resorbable cements, or precursors to resorbable cements or some combination thereof.

Antibiotic additives may include any suitable antibiotic, or antibiotic combinations, such as, but not limited to, demeclocycline, doxycycline, minocycline, oxytetracycline, tetracycline, thiamphenicol, ciprofloxacin, enoxacin, gatifloxacin, levofloxacin, lomefloxacin, moxifloxacin, nalidixic acid, norfloxacin, ofloxacin, bacitracin, colistin, amoxicillin/clavulanate, ampicillin/sulbactam, piperacillin/tazobactam, ticarcillin/clavulanate, or some combination thereof.

In a preferred embodiment, the ink may, for instance, be supplied in the form of a precursor powder 190 and a precursor liquid 195. These may be feed to separate containers in the 3-D printer. Prior to printing, a quantity of the precursor powder 190 and the precursor liquid 195 may be mixed to form the ink 150 to be used for printing the custom bone graft 120. The printing may be accomplished by delivering quantities of the ink 150 via a suitably sized print nozzle 235 that may be moved in a raster scan 230 with respect to the custom bone graft 120 being printed.

The precursor powder 190 of the ink 150 may, for instance, contain a variety of ingredients such as, but not limited to, demineralized allograft bone matrix (DMB) 145, sucrose crystals 170, radical polymerization initiator 175 or some combination thereof.

The radical polymerization initiator 175 may, for instance, be a compound such as, but not limited to, di-benzoyl peroxide (BPO).

The precursor liquid 195 may for, instance, contain a variety of ingredients such as, but not limited to, methyl methacrylate (MMA) 165, a radio-pacifier 185, an antibiotic 180, and a compound to increase the biodegradability 265, or some combination thereof.

The radio-pacifier 185 may, for instance, be a compound such as, but not limited to, zirconium dioxide ($ZrO_2$) or barium sulphate ($BaSO_4$) or some combination thereof.

The antibiotic 180 may, for instance, be a compound such as, but not limited to, amoxicillin, doxycycline, gentamicin or clindamycin or some combination thereof.

The compound to increase the biodegradability 265 may, for instance, be a compound such as, but not limited to, cellulose acetate (CA), or cellulose acetate phthalate (CAP) or some combination thereof.

Figure 7:
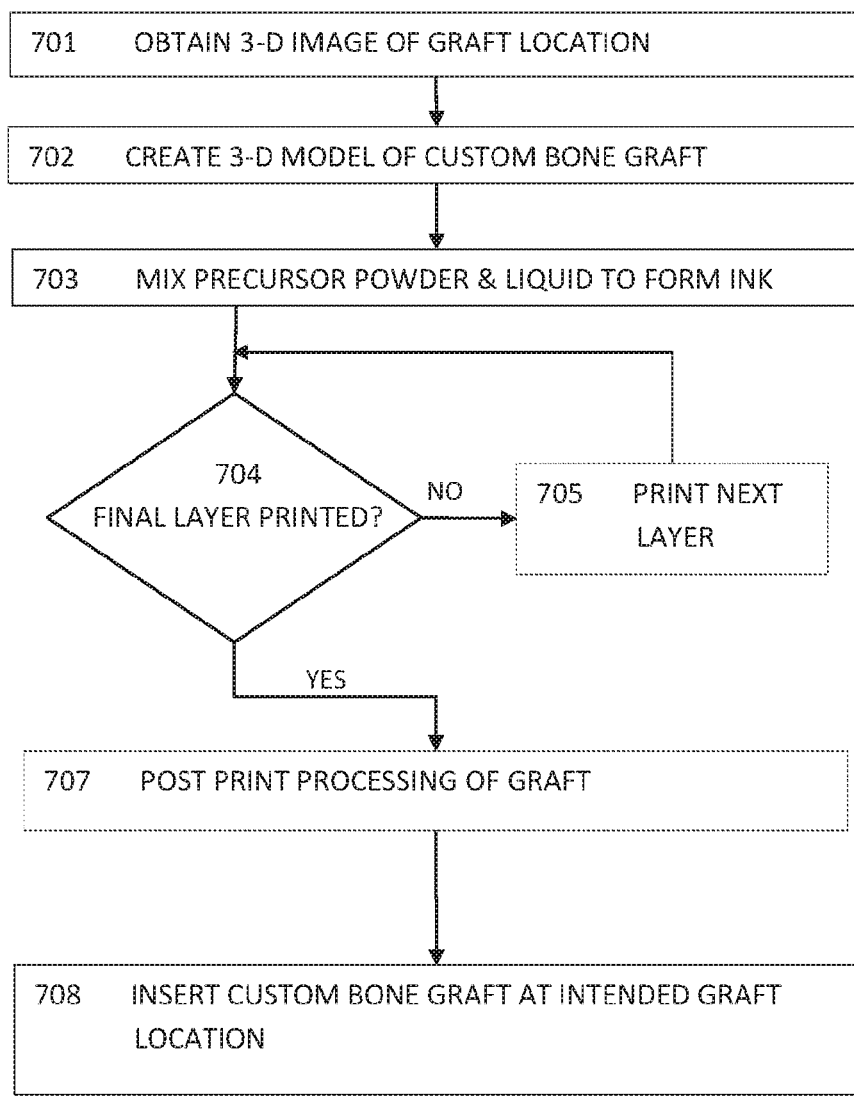
FIG. 7 shows a sematic flow diagram of representative steps of a preferred embodiment of the present invention.

FIG. 7 shows a sematic flow diagram of representative steps of a preferred embodiment of the present invention.

In Step 701 "Obtain 3-D Image of Graft Location", the patient may be imaged using one of a number of well-known techniques for obtaining a 3-D image such as, but not limited to, a cone beam 3-D camera, computer aided tomography, 3-D laser cameras, CT scan, or a combination thereof.

In Step 702 "Create 3-D Model of Custom Bone Graft", the images obtained in step 701 may be used by a suitably constructed computer program operable on a suitable digital data processor, to generate a 3-D model of a custom bone graft for the patient. In this step, the computer program may also use a database of standard models of human body parts to provide guidance on areas that may not be adequately described or detailed by the 3-D images. The bone graft may be modeled on the water tight 3-D mesh created as the supporting scaffold to give the user an insight as to the overall size, bulk, weight, etc. The term "water tight" is generally used to mean the mesh bears no holes, cracks or missing features.

The custom bone graft may also include provision for locating fixation screws that might be added using guidance from a qualified professional. Further, using the 3-D model, one may be able to plan or distribute the screws required as to avoid anatomical structures, friction, or other undesirable side effects from the screws. Fixation screws, including their size, location and orientation may be designed on the computer model by a competent expert. In other embodiments, the software or program automatically positions such screws and their desired position can be then confirmed by the doctor. Holes for drill sleeves may then be designed into the custom bone graft by the suitably constructed computer program for doctor approval. Sleeves may then be inserted into the bone graft. The surgeon may then be supplied with directions and the drill size and depth required for each fixation screws by the software or program. The drill may, for instance, incorporate a stop to prevent it penetrating too deeply into the bone of the graft recipient, or into vital structures within the bone such as, but not limited to, arteries, veins or nerves. Once the holes are drilled, the sleeves may be removed and the fixation screws inserted by the surgeon to hold the graft in place. The fixation screws may for instance be made of stainless steel, titanium or resorbable screws, and may be supplied with the graft.

In Step 703 "Mix Precursor Powder & Liquid to Form Ink", precursors of the ink may be mixed in relatively small batches. The size of the batches mixed into ink may depend on the print speed of the 3-D printer, the print nozzle size of the printer, and the constituents of the precursors, as once mixed, the ink will begin to polymerize with the viscosity of the ink increasing with time. Only as much ink as may be used by the 3-D printer in the time the ink is deliverable by the print nozzle may be mixed at any one time. In some embodiments, preset ink or printing medium is supplied to the user.

The software or program may select a particular size syringe, as described above, for use in the printing process. Once printing is ready to begin, steps can be taken to ensure the printing process occurs under sterile conditions. A protective hood will enclose the printing area and air brought into the enclosed environments will be subjected to filtration by a medical grade HEPA filter. Air can further be removed from the enclosed area via a surgical vacuum.

As it is being printed, the mesh itself may be moved or rotated in relation to a position of the printing nozzle. Preferably, when using an extrusion process (to melt or soften rods of printing medium) the operating or printing temperature of this scaffold is about 60 degrees Centigrade to about 120 degrees Centigrade depending on the exact material or combination of materials chosen.

The printing temperature may also be selected in response to the desired size of the print string to be deposited and/or the size of the aperture on the head of the printing nozzle. In some embodiments, such parameters can be customized by the user, whereas in other embodiments the 3-D printer receives an input as to the desired parameters (print string size, print medium, etc.) and the 3-D printer calculates the operating parameters such as temperature, print speed, etc.

Further, some grafts and/or implants may be sizable when compared to other implants and/or grafts. Such grafts and/or implants may need some element of reinforcement. For example, the mesh or scaffold may be printed around a titanium rod. The rod may be situated in such a way that permits removal of the rod after implantation (and sufficient cell/bone growth) or may simply be configured to remain within the newly grown bone. Overall, the layers are continually printed until the 3-D printer determines that the final layer has been reached.

In Step 704 "Final Layer Printed?" the 3-D printer may first check to see if it has printed all the layers required to produce the custom bone graft. These layers may have been provided by a programmed module operative on a digital data processing device, and may be the 3-D model of the custom bone graft reduced to consecutive slices that printed in the correct order may result in the required custom bone graft.

In Step 705 "Print Next Layer", the 3-D printer may, if the final layer has not yet been printed, print the next layer. This may be done by, for instance, moving the print nozzle in a raster fashion, depositing ink where required. The printing is preferably performed in a sterilized environment as noted above.

In Step 707 "Post Print Processing of Graft", once the 3-D printer has printed all the required layers that constitute the custom bone graft, the bone graft may undergo post print processing. Initially, the graft needs to be separated from the printing plate. This post processing step may also, for instance, include actions such as, but not limited to, dissolving out the sucrose crystals to provide a porous structure and sterilization of the custom bone graft, infusing graft with allograft, xenograft, antibiotics, BMPs, or other materials to ensure reception and stimulate bone growth. In some embodiments such additives are done at the printing stage by a multi-headed printer having such materials contained in varying syringes or holding containers.

In Step 708 "Insert Custom Bone Graft at Intended Graft Location" the printed and processed custom bone graft may now be inserted into the patient at the intended graft location. The recipient site is exposed and the scaffold or graft can then be inserted into the recipient site. The doctor may use the predetermined drills into the pilot holes in the graft. Metal or resorbable screws may be used to fix a position of the graft. Further, the screws may be color coded and the color of the screws may be selected by the software. Once the position is fully secured, primary closure is completed and the surgery can then be resolved.

In alternate embodiments, the ink may include demineralized xenograft bone, synthetic bone substitutes, and other slow reabsorbing biocompatible, bioactive adhesives.

Alternate formulations of the printing ink may, for instance, include artificial bone substitutes such as, but not limited to, hydroxyapatite, synthetic calcium phosphate ceramic. These may be used instead of, or with natural bone particulates such as, but not limited to, allograft particulate bone, or xenograft particulate bone, or some combination thereof. These may, for instance, be used with synthetically produced bone morphogenetic agents such as, but not limited to, recombinant human Bone Morphogenetic Protein-2 (rhBMP-2).

Alternate inks may also, or instead, use other biocompatible, bio-active adhesives such as, but not limited to glass polyalkenoate cements, oleic methyl ester based adhesives, or some combination thereof.

Although producing the custom bone grafts has been discussed with respect to 3-D printing, some or all of the machining of the custom bone grafts may be done using more conventional machining such as computer numerical control (CNC) milling, drilling or routing machines. The holes for the fixation screws may, for instance, be drilled by CNC machine after the custom graft is produced, or support structure necessary during the printing of a complex shape may be removed by CNC machining, or a starting template may be CNC machined from natural or synthetic bone material to reduce the printing time of the entire custom graft.

In order to do such machining the digital processor 240 may generate a 3-D model in a suitable computer language such as, but not limited to, G-code that may enable a CNC machine to machine a block of bone substitute material. The block of bone material may, for instance, be a material such as, but not limited to, REPROBONE® material as supplied by Ceraymisys, Ltd. of Sheffield, England. The material used to create the custom bone graft may also, or instead, be a calcium phosphate material such as, but not limited to, hydroxyapatite.

In a preferred embodiment, the machining may, for instance, be accomplished using a multi-axis CNC milling machine such as, but not limited to, a LAVA™ CNC 500 milling system manufactured by 3M of Minneapolis, Minn.

In a further preferred embodiment of the invention, a semipermeable, resorbable membrane may be printed on top of the bone graft using a second ink. Such a membrane may, for instance, be made of a co-polymeric blend of poly-vinyl alcohol (PVA) and poly-vinyl pyrrolidone (PVP), as discussed in, for instance, U.S. Pat. No. 7,476,250 issued to Mansmann on Jan. 13, 2009 entitled "Semi-permeable membranes to assist in cartilage repair", the contents of which are hereby incorporated by reference. The semipermeable, resorbable membrane may, for instance, be extend beyond the perimeter of the bone graft in some or all portions of the perimeter, by an amount that may be as much as 1 cm, but is more preferably 0.5 cm.

In yet a further preferred embodiment of the invention, a custom bone graft 120 may be produced using a graft negative mold 305. The graft negative mold 305 may, for instance, be generated using a 3-D digital graft model 310 produced from a 3-D image 105 obtained using a X-ray imaging machine 155 such as, but not limited to, a cone-beam X-ray imaging machine 315.

Figure 8:
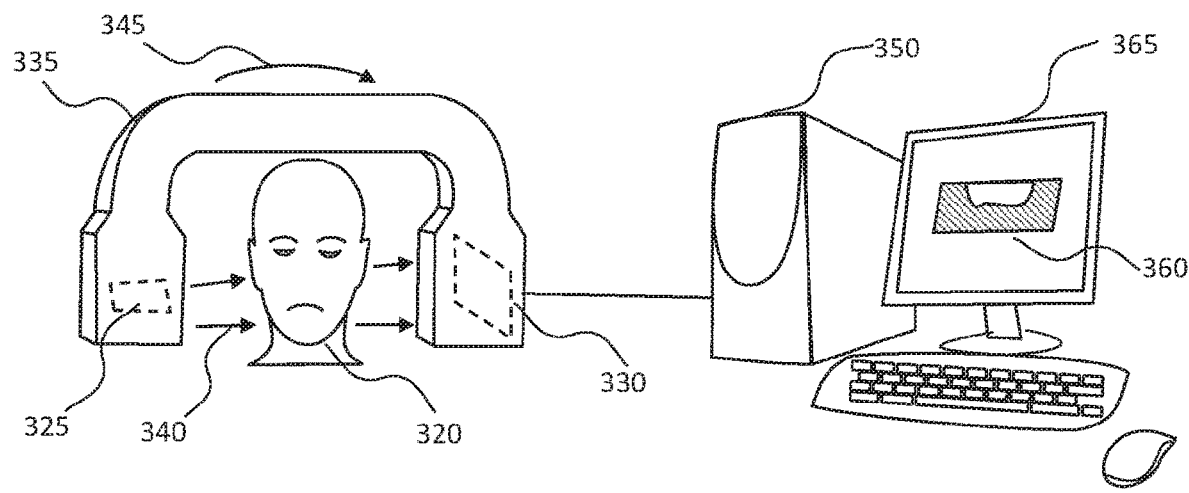
FIG. 8 shows a cone-beam scan of a patient used by computer software to produce an image of a bone defect.

FIG. 8 shows a cone-beam X-ray imaging machine 315 to perform a scan of a patient 320. A cone-beam X-ray imaging machine 315 typically contains an X-ray generator 325 and a digital X-ray sensor 330. The X-ray generator 325 and the digital X-ray sensor 330 may, for instance, be housed at opposite extremities of a C-shaped housing 335. The X-ray generator 325 may emit a conical beam of X-rays 340 as the C-shaped housing 335 is rotated 345 around the patient 320. The data captured by the digital X-ray sensor 330 may then be sent to a digital computer 350 that may be running suitable software to convert that data into a 3-D image 360 of a bone defect 355 aka an intended graft location 370. The 3-D image 360 of a bone defect may, for instance, be displayed on a digital display 365.

Figure 9:
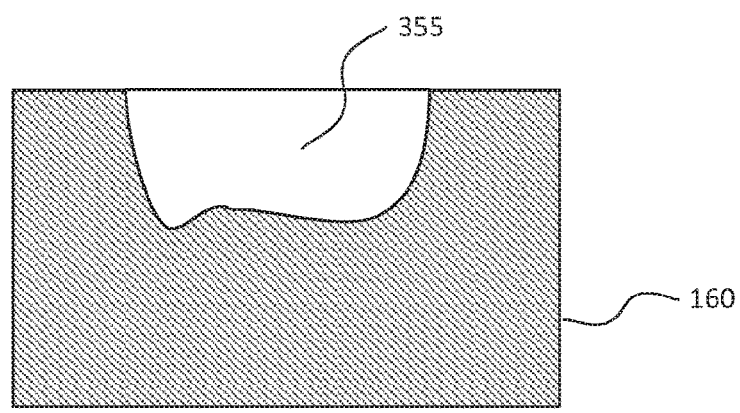
FIG. 9 shows a sectional view of a 3-D reconstruction of an imaged defect.

FIG. 9 shows a sectional view of a 3-D image 360 of a bone defect such as, but not limited to, bone and/or cartilage tissue lost to trauma, surgery, infection, normal aging or anatomic abnormalities due to any pathology. This method may, for instance, be useful in oral maxillofacial surgery, dental implants, orthopedic surgery or any type of reconstructive hard tissue surgery.

Figure 10:
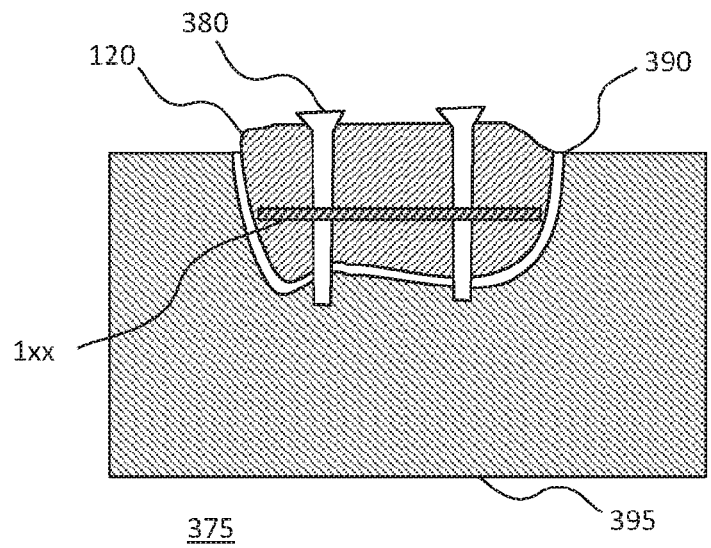
FIG. 10 shows a sectional view of a computer generated 3-D positive image of a required graft.

FIG. 10 shows a sectional view of a computer generated 3-D positive image 375 of a required custom bone graft 120 to be located at a bone site 395.

In a preferred embodiment, the 3-D positive image 375 of a required custom bone graft may also include additional requirements such as, but not limited to, any required locating screws 380, or guide paths for screws or tacks to fix the graft in place, space for adhesive 385 and any required structural reinforcement 390, or guide holes to accommodate reinforcement pins, or some combination thereof.

Figure 11:
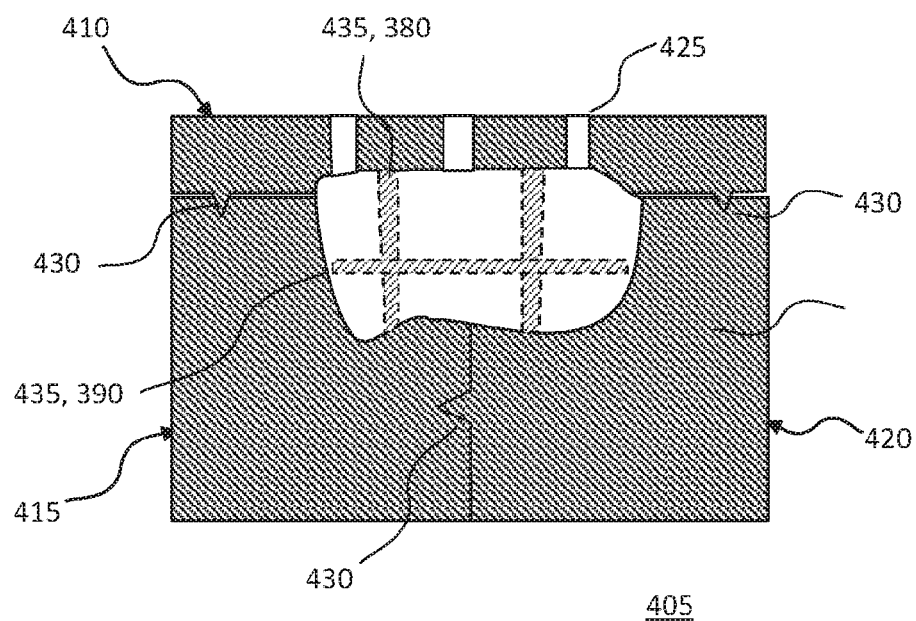
FIG. 11 shows a sectional view of a negative mold of a required graft.

FIG. 11 shows a sectional view of a computer generated model of a negative mold 405 of a required graft. The negative mold 405 may, for instance, include a top of a negative mold 410, a left bottom of a negative mold 415, and a right bottom of a negative mold 420, or some combination thereof. The negative mold 405 of a required graft may, for instance, include suitable relief vent holes 425, locating cones 430, or some combination thereof. The top of a negative mold 410 may, for instance, be also include suitable locating keys 435 or guide paths for additions such as, but not limited to, locating screws or tacks 380, structural reinforcement pins 390 or some combination thereof.

In a preferred embodiment, the negative mold 405 of a required graft may be made using a 3-D printer and suitable polymers or photopolymers. The negative mold 405 of a required graft may also be made, wholly or in part, using a CNC machine such as, but not limited to, a CNC router, or a combination of 3-D printing and CNC machining.

Figure 12:
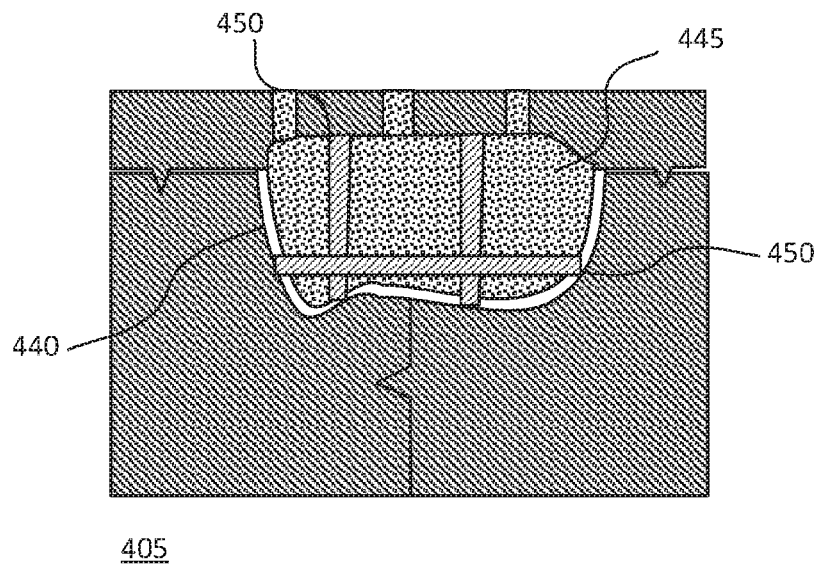
FIG. 12 shows a sectional view of a negative mold being used to produce a required graft.

FIG. 12 shows a sectional view of a negative mold being used to produce a required graft. The negative mold 405 of a required graft may, for instance, be first coated with a suitable release agent 440 and any necessary place holders 450 for any structural reinforcement 390 or locating screws 380 or a combination thereof. An FDA approved, porous, biodegradable, biocompatible material 445 that is conducive to osteoinduction and has a load bearing strength comparable to bone, to produce said custom bone graft may then be poured, placed or inserted into the negative mold 405 of a required graft.

The materials used in producing the customized bone graft from the negative mold may include any of the appropriate materials, and combinations of materials, described above such as, but not limited to, demineralized allograft bone matrix (DMB), or porous Poly Methyl Methacrylate (PMMA) 140 and recombinant human Bone Morphogenetic Protein-2 (rhBMP-2), or some combination thereof.

In a preferred embodiment of the present invention, the material may be a mixture such as, but not limited to, Calcium Sulfate hemihydrate, aka Plaster of Paris, demineralized freeze dried bone (DFDB), or freeze dried bone (FDB), Bone Morphogenetic Proteins (BMP) and an antibiotic such as, but not limited to, Odxucicline.

Further materials including, but not limited to, solidifying resorbable or non resorbable possibly osteoconductive, osteoinductive medium that may be placed inside the negative mold. Such a medium may, for instance, be a medium such as, but not limited to, polymethylmethacrylate (PMMA), Fibrin Glue, Hydroxyapatite cements or Bio-glass or some combination thereof. Other biomaterials such as, but not limited to, coral, bone-derived materials, bioactive glass ceramics, and synthetic calcium phosphate that may have been mixed with fibrin sealant bone grafting material that may be added by an operator (any particulate material available may function) as well as BMPs, antibiotics or other additives deemed necessary. Material that may be in excess of the required amount may be placed so as to accommodate any resorption of the graft. The negative lid may be placed by, for instance, guiding cones that may engage negative mold cone holes. Excess material may be squeezed out of the negative lid through suitably place relieve vents and be removed while the bone graft is still in a gelatinous, or liquid state.

The porous, biodegradable, biocompatible material 445 may be allowed to, or induced to, set, thereby creating a required custom bone graft 120.

Figure 13:
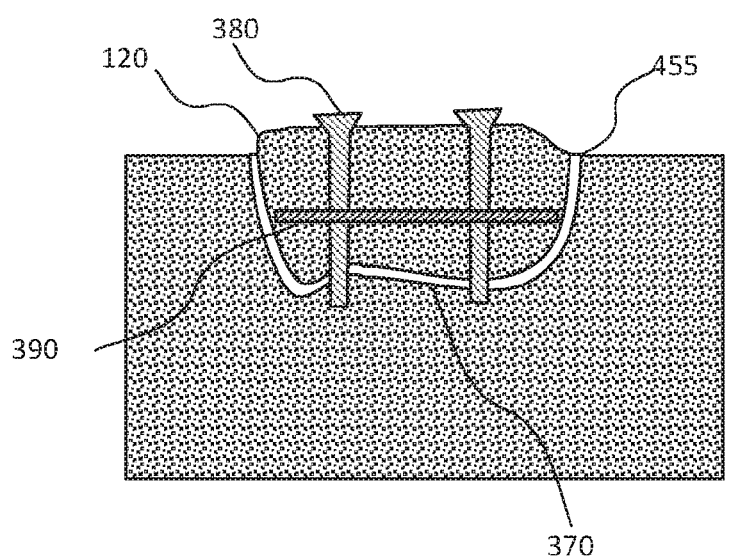
FIG. 13 shows a sectional view of a graft being placed during surgery.

FIG. 13 shows a sectional view of a graft being placed during surgery. The intended graft location 370 may first be coated with a bone adhesive 455. The custom bone graft 120, including any necessary structural reinforcement 390 that may be incorporated into it, may then be placed in the intended graft location 370. The custom bone graft 120 may then be secured in the intended graft location 370 by a suitable means such as, but not limited to, one or more locating screws 380 or tacks, that may be bio-inert and may be bio-absorbable. The structural reinforcement 390 and locating screws 380 are preferably biocompatible and may be biodegradable. Suitable biocompatible materials include compositions such as, but not limited to, plastics such as PMMA and stainless steel, polygluconate co-polymer (PGACP) or self-reinforced poly-L-lactic acid polymer (PLLA) or some combination thereof.

FIGS. 14A-D are illustrative of steps that may be used in the process of fabricating a required complex long bone graft 460.

FIG. 14A shows a required complex long bone graft that may be required 460.

Figure 14:
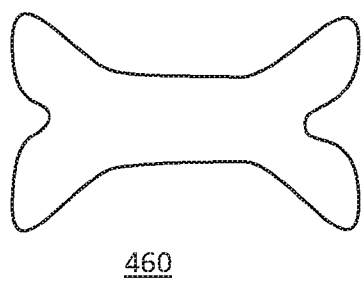
FIG. 14A shows a required complex long bone graft.
FIG. 14B shows a negative mold for a portion of the required complex long bone graft.
FIG. 14C shows a negative mold being used to produce a portion of the required complex long bone graft.
FIG. 14D shows a negative mold being used to produce a portion of the required complex long bone graft.
Figure 14:
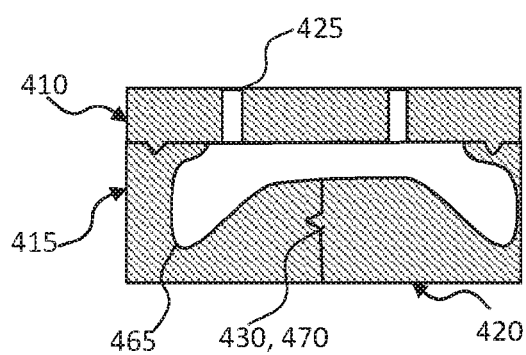
Figure 14:
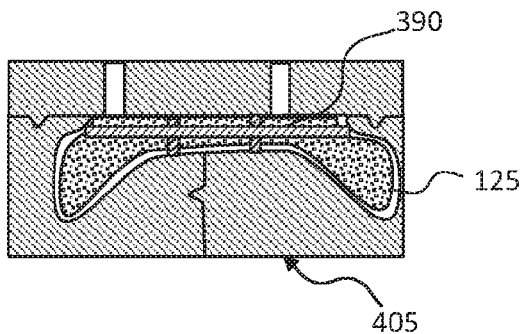
Figure 14:
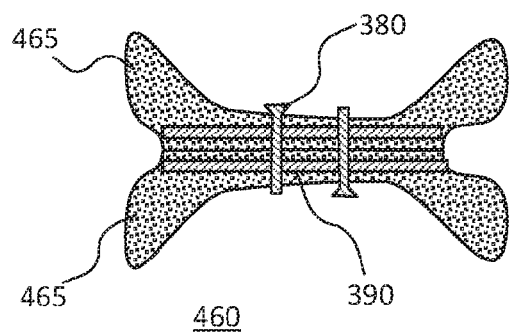

FIG. 14B shows a negative mold for a portion 465 of the required complex long bone graft 460. In the instance shown in FIG. 14 B, the negative mold is designed to produce one half of the bone graft. The negative mold may include a top of a negative mold 410, a left bottom of a negative mold 415 and a right bottom of a negative mold 420 as well as locating cones 430 and corresponding locating indents 470, and vent holes 425.

FIG. 14C shows a negative mold being used to produce a portion of the required complex long bone graft. The negative mold 405 of a portion of the required graft, containing any required structural reinforcement 390, may have been coated with a suitable release agent and then filled with an appropriate porous, biocompatible material 125.

FIG. 14D shows a complex long bone graft 460 composed of two portions 465 of the bone graft that may contain structural reinforcements 390 and held together by one or more locating screws 380.

Figure 16:
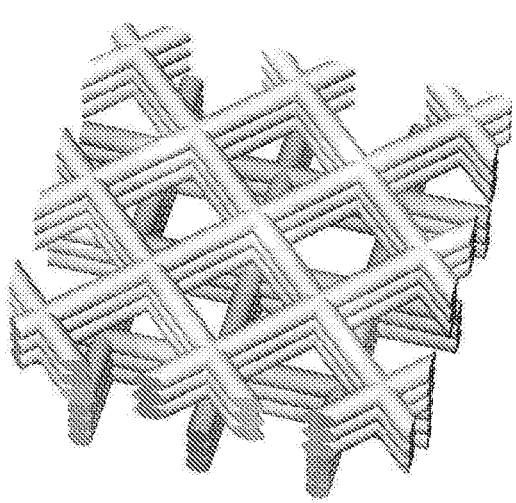
FIG. 16A illustrates a porous grid printed with a layer rotation methodology.
FIG. 16B illustrates a porous grid printed with a layer sidestepping methodology.
FIG. 16C illustrates a sectional side view of an interconnection of a porous grid.
Figure 16:
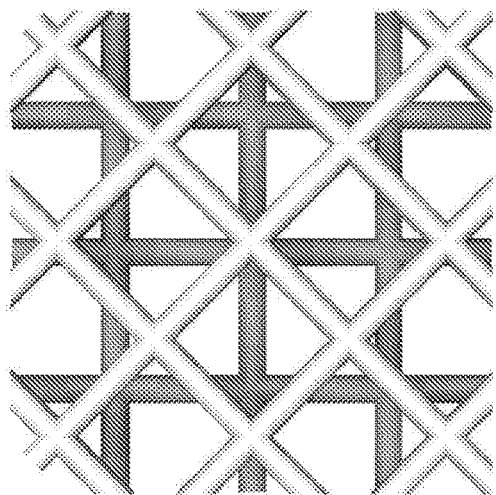
Figure 16:
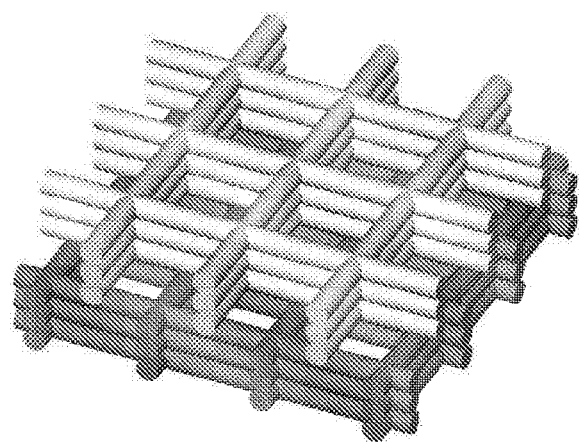
Figure 16:
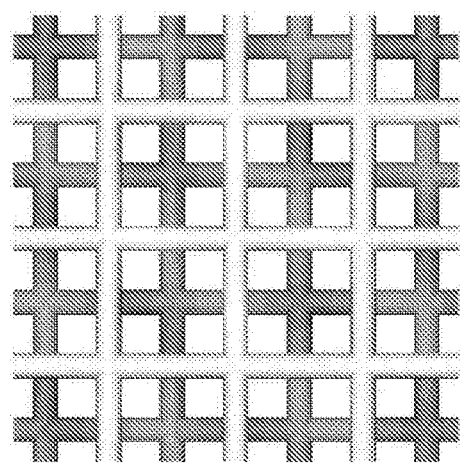
Figure 16:
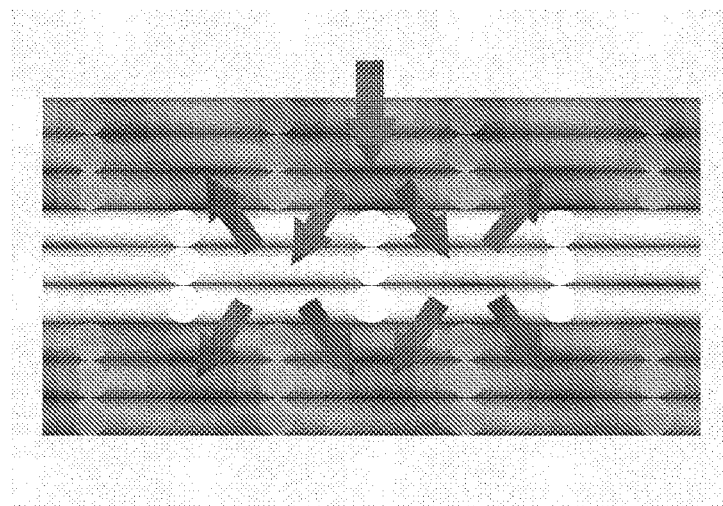

Referring now to FIGS. 16A and 16B, there are illustrations demonstrating at least two potential printing methodologies for the scaffold or mesh construction. In FIGS. 16A-B, there is a perspective and top view of a rotation printing methodology. In FIG. 16C, there is a side view of a sidestepping printing methodology demonstrating an interconnection of a porous grid.

In FIG. 16A, the layers are shown to be printed with three layers aligned with one another forming single tier and three layers rotatably shifted and aligned with one another forming alternating tier. The two sets of directionally positioned layers are situated upon one another. The number of layers comprising each "layer" before the rotation occurs may vary and may be from about one layer to about twenty five layers. The amount of rotation may also vary and is preferably at least 45.degree. in relation to the layer(s) located below the layers of rotation.

In FIG. 16B, the layers are shown to be printed with three layers aligned with one another forming single tier and three layers shifted forming alternating tier. Here, the layers have not been rotated but the connection points forming the lattices have been shifted in relation to a predetermined "layering" of the printing medium. As shown, the bottom three layers and the top three layers are aligned in terms of printing pattern with the connection points of the lattices aligned with one another. The middle three layers have these connection points shifted to be somewhere within the distance formed between a first set and a second set of connection points. The spacing of the connection points and the location of the interspersed (shifted) layers between these points may vary as desired. As described above, the number of layers may also vary as desired.

Preferably, there are alternating tiers layered on top of each other until they fill graft vertically. Horizontal form of the graft is printed based on form of the 3D model.

Each of the above printing methodologies outlined in FIGS. 16A-B, and others not explicitly described herein, are configured and designed to promote maximum vascular and neural growth within the graft (see FIG. 16C). This allows full vascular and neural penetration in to the grafting material which is disposed on to the rigid scaffold or mesh described herein.

Although this invention has been described with a certain degree of particularity, it is to be understood that the present disclosure has been made only by way of illustration and that numerous changes in the details of construction and arrangement of parts may be resorted to without departing from the spirit and the scope of the invention.

We claim:

1. A method for producing a custom bone graft, comprising:
   obtaining a three-dimensional image of an intended graft location;
   creating a three-dimensional mesh using said three-dimensional image, wherein said created three-dimensional mesh serves as a supporting scaffold for said custom bone graft;
   creating a three-dimensional digital model of said custom bone graft using said three-dimensional image;
   creating a printing medium, wherein said printing medium comprises a mixture of a precursor powder and a precursor liquid in a predetermined ratio, and wherein a slow reabsorbing biocompatible, bioactive adhesive is added to said printing medium for improving fixation of said custom bone graft at said intended graft location;
   creating, by a three-dimensional printer, said custom bone graft, using said three-dimensional digital model, said created three-dimensional mesh, and said printing medium, wherein said printing medium is deposited layer by layer on a sterile disposable print surface, wherein after printing a predetermined number of layers, the three-dimensional mesh is one of rotated and side-stepped before printing next set of the predetermined number of layers, wherein said rotation and side-stepping processes promote maximum vascular and neural growth within said created custom bone graft, wherein said creation of said custom bone graft is performed in a sterile environment comprising:
   said sterile disposable print surface;
   a sterile syringe for injecting said printing medium;
   a hood enclosing said three-dimensional printer, wherein said hood is coupled to a medical grade high efficiency particulate air filter, and wherein sterile air is drawn into said hood via said high efficiency particulate air filter and removed via a surgical-type suction connection; and
   wherein said sterile custom bone graft is adapted for direct insertion at said intended graft location without additional sterilization procedure.

2. The method of claim 1, wherein said precursor powder comprises demineralized allograft bone matrix, and said precursor liquid comprises poly methyl methacrylate.

3. The method of claim 2, wherein said demineralized allograft bone matrix comprises collagen and bone morphogenetic proteins.

4. The method of claim 1, wherein said precursor powder comprises demineralized allograft bone matrix, sucrose crystals and a radical polymerization initiator, and wherein said precursor liquid comprises methyl methacrylate.

5. The method of claim 4, wherein said radical polymerization initiator comprises di-benzoyl peroxide.

6. The method of claim 4, wherein said precursor liquid further comprises an antibiotic.

7. The method of claim 6, wherein said antibiotic comprises one of amoxicillin, doxycycline, gentamicin and clindamycin, or some combination thereof.

8. The method of claim 4, wherein said precursor liquid further comprises a radio-pacifier.

9. The method of claim 8, wherein said radio-pacifier comprises one of zirconium dioxide, barium sulphate, or any combination thereof.

10. The method of claim 1, wherein said precursor liquid further comprises a compound to increase biodegradability of said printing medium, and wherein said compound comprises cellulose acetate, cellulose acetate phthalate, or any combination thereof.

11. The method of claim 1, wherein said printing medium comprises polycaprolactone, polylactic acid, polylactic-co-glycolic acid, or any combination thereof.

12. A method for producing a custom bone graft, comprising:
   obtaining a three-dimensional image of an intended graft location;
   creating a three-dimensional digital model of said custom bone graft using said three-dimensional image;
   creating, by a three-dimensional printer, said custom bone graft, using said three-dimensional digital model and a printing material, wherein said printing material is a solid rod that is melted and deposited layer by layer by an extrusion deposition method, wherein after printing a predetermined number of layers, the print axis is one of rotated and side-stepped before printing next set of the predetermined number of layers, wherein said rotation and side-stepping processes promote maximum vascular and neural growth within said created custom bone graft, wherein said creation of said custom bone graft is performed in a sterile environment comprising:
   a sterile disposable print surface;
   a sterile syringe for injecting said printing medium;
   a hood enclosing said three-dimensional printer, wherein said hood is coupled to a medical grade high efficiency particulate air filter, and wherein sterile air is drawn into said hood via said high efficiency particulate air filter and removed via a surgical-type suction connection; and
   wherein said sterile custom bone graft is adapted for direct insertion at said intended graft location without additional sterilization procedure.

13. The method of claim 1, wherein said printing material comprises solidifying resorbable or non resorbable, osteoconductive, osteoinductive material.

* * * * *